United States Patent [19]

Smith et al.

[11] Patent Number: 5,039,803

[45] Date of Patent: Aug. 13, 1991

[54] PROCESS FOR PREPARING ARYL-SUBSTITUTED PIPERIDINES

[75] Inventors: Paul Smith; Gillian E. Smith, both of Harlow, England

[73] Assignee: Beecham Pharmaceuticals, Essex, England

[21] Appl. No.: 424,157

[22] Filed: Oct. 19, 1989

[51] Int. Cl.$^5$ .................................. C07D 211/14
[52] U.S. Cl. .................................................. 546/185
[58] Field of Search ........................................ 546/185

[56] References Cited

FOREIGN PATENT DOCUMENTS 219934  4/1987  European Pat. Off. ............ 546/185
1537867 1/1979  United Kingdom ................ 546/185

OTHER PUBLICATIONS

March, J., *Advanced Organic Chemistry*, McGraw Hill, New York, 1968, p. 892.

*Primary Examiner*—Mary C. Lee
*Assistant Examiner*—Jacqueline Haley
*Attorney, Agent, or Firm*—Hopgood, Calimafde, Kalil, Blaustein & Judlowe

[57] ABSTRACT

A process for preparing a compound of formula (I):

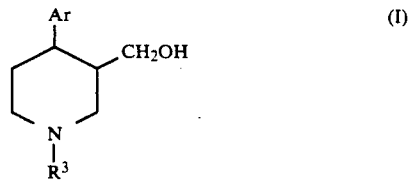

in which Ar represents an aryl or substituted aryl group and $R^3$ represents an alkyl group, which comprises reducing a compound of formula (II):

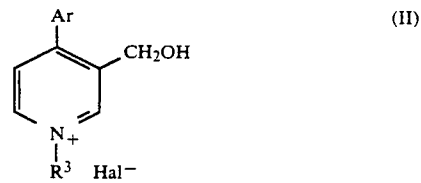

in which Ar and $R^3$ are as defined for formula (I), and Hal represents a halogen atom.

7 Claims, No Drawings

PROCESS FOR PREPARING ARYL-SUBSTITUTED PIPERIDINES

This is a continuation-in-part of Ser. No. 209,873 filed on June 22, 1988, now abandoned.

This invention relates to a novel chemical process for preparing aryl-piperidine carbinols and to novel intermediates used in that process.

British Pat. No. 1422263 and U.S. Pat. No. 4,007,196 disclose compounds of formula (A):

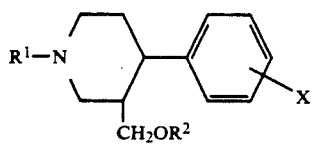

in which $R^1$ represents hydrogen, trifluoro ($C_{1-4}$) alkyl, alkyl or alkynyl, $R^2$ represents an alkyl or alkynyl group having 1-4 carbon atoms, or a phenyl group optionally substituted by $C_{1-4}$ alkyl, alkylthio, alkoxy, halogen, nitro, acylamino, methylsulfonyl or methylenedioxy, or represents tetrahydronaphthyl, and X represents hydrogen, alkyl having 1-4 carbon atoms, alkoxy, trifluoroalkyl, hydroxy, halogen, methylthio, or aralkyloxy.

The compounds of formula (A) are disclosed as having pharmacological properties that make them useful as antidepressants. One compound that has proved especially valuable is paroxetine ($R^1=H$, $R^2=5$-(1,3-benzdioxolyl), $X=4-F$) which is in the (−)-trans configuration.

In the above-mentioned patents, the compounds of formula (A) are prepared using an intermediate of formula (B):

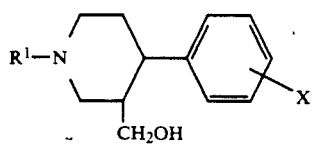

in which $R^1$ and X are as defined above.

The piperidine carbinols of formula (B) are prepared by reducing an ester of formula (C):

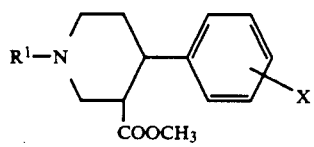

with a complex metal hydride reducing agent.

The compound of formula (C) is obtained by reacting arecoline (when $R^1=$methyl) or arecoline analogues with phenyl (or substituted phenyl) magnesium bromide. This procedure has the disadvantage that arecoline is a powerful irritant and that the ester of formula (C) is obtained as a mixture of cis and trans configuration compounds.

We have now discovered a new process for the preparation of piperidine carbinols which advantageously avoids the use of arecoline and selectively produces the cis-isomer.

Accordingly, the present invention provides a process for preparing a compound of formula (I):

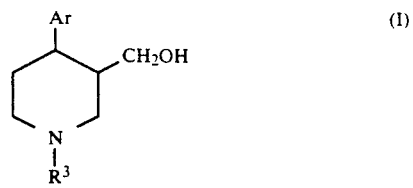

in which Ar represents an aryl or substituted aryl group and $R^3$ represents an alkyl group, by reducing a compound of formula (II):

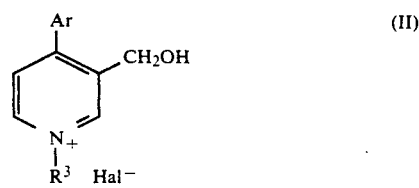

in which Ar and $R^3$ are as defined for formula (I), and Hal represents a halogen atom.

In formulae (I) and (II), Ar may be phenyl optionally substituted by one or more groups selected from hydrogen, $C_{1-6}$ alkyl, $C_{1-6}$ alkoxy, trifluoro $C_{1-6}$ alkyl, hydroxy, halogen, methylthio or phenyl $C_{1-6}$ alkyloxy. Preferably Ar represents fluorophenyl, more preferably 4-fluorophenyl. $R^3$ is preferably methyl, and Hal is preferably chlorine or bromine.

The reduction may be carried out in a single reaction by catalytic hydrogenation, for example using a platinum oxide catalyst at atmospheric pressure.

Alternatively, a stepwise procedure may be followed in which reduction with, for example sodium borohydride, gives a compound of formula (III):

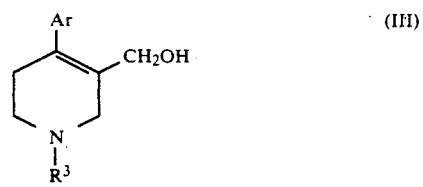

in which Ar and $R^3$ are as defined for formula (I), which is then further reduced by catalytic hydrogenation to give a compound of formula (I).

Accordingly in a further aspect of the invention there is provided a process for preparing a compound of formula (I) by reduction of a compound of formula (III) in which Ar and $R^3$ are as defined for formula (I).

The compounds of formula (I) are obtained in the cis-configuration but as a mixture of enantiomers. The compounds may be resolved into their enantiomeric forms by conventional methods such as by use of an optically active acid.

The compounds of formula (I) may be used as intermediates in the preparation of compounds of formula (A) making use of procedures set out in U.K. Pat. No. 1422263 or U.S. Pat. No. 4,007,196.

For example, to prepare paroxetine, the carbinol in which Ar is 4-fluorophenyl and $R^3$ is methyl in the (+)-cis configuration is reacted with thionyl chloride or benzenesulphonyl chloride and then with sodium 3 4-methylenedioxyphenoxide. Subsequently the N- methyl group is replaced by reaction with phenyl chloroformate followed by de-acylation with KOH to obtain the compound in which $R^3$ is hydrogen.

The present invention also provides the intermediates of formula (II) as novel compounds. Preferred substituents are as exemplified for formula (I).

The quaternary pyridines of formula (II) may be prepared from 3-pyridyl carbinol compounds of formula (IV):

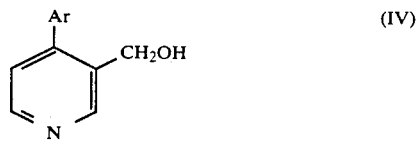

in which Ar is as defined for formula (I), by quaternisation under conventional conditions with an alkyl halide of formula $R^3$-Hal in which $R^3$ is as defined for formula (I) and Hal is a halogen atom.

The compounds of formula (IV) may be prepared by reducing a 3-pyridinecarboxaldehyde of formula (V): in which Ar is as defined for formula (I), preferably with sodium borohydride under conventional conditions, for example in methanol at reduced temperatures.

The compounds of formula (V) may be obtained by reaction of a methyl styrene compounds with oxalyl chloride according to the method of C. Jutz, W. Muller and E. Muller, Chem. Ber., 1966, 99, 2479.

Certain of the intermediates described above are novel and, together with the above described processes for their preparation, they form part of the present invention.

In particular the present invention provides as novel compounds the compounds of formula (III) in which Ar and $R^3$ are as defined for formula (I).

As used herein, the terms alkyl, alkoxy, aralkyloxy and aryl include, but are not limited to, groups in which the alkyl moiety, when present, is a straight or branched alkyl group containing from 1 to 6 carbon atoms, more especially from 1 to 4 carbon atoms, and the aryl moiety, when present, is phenyl.

The following examples illustrate the preparation of novel intermediates (Examples 1,2,3 and 5) and the novel process of this invention (Examples 4 and 5).

Example 1

4-p-Fluorophenyl-3-formylpyridine hydrochloride

The title compound was prepared following the method described in the literature (C. Jutz, W. Muller and E. Muller, Chem. Ber., 1966 99, 2479) for 3-formyl-4-phenylpyridine.

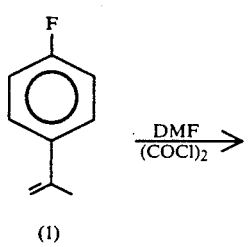

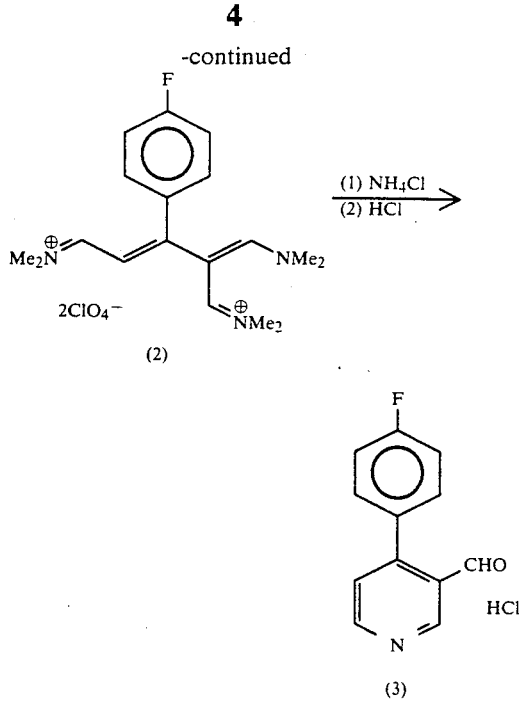

Oxalyl chloride (34 ml; 0.39 moles) was added to a stirred solution of dimethylformamide (33 ml; 0.42 moles) in 1,2-dichloroethane (50 ml). To the resulting mixture was added α-methyl-p-fluorostyrene (13.6 g; 0.1 moles) in dichloroethane (20 ml) and the mixture refluxed for 3 hours. After removal of solvent by distillation under reduced pressure, water (150 ml) was added to give a dark brown solution. An aqueous solution of sodium perchlorate was added to this solution causing the di-iminium perchlorate (2) to precipitate. This was filtered off, washed with water, added to an aqueous solution of ammonium chloride (24 g in 190 ml of water) and heated at 100° C. for 1 hour. After allowing to cool, the reaction mixture was extracted with chloroform and the organic layer separated, washed with water, and ethereal HCl added causing the title compound (3) to precipitate as buff coloured crystals (18g; 76% yield based on styrene (1))

m.p.: 200–205° C.

nmr (DMSO): δ10.0, (s), 1H δ9.05, (s), 1H δ8.92, (d, J=5Hz), 1H δ7.85–7.38, (m), 5H M/e: 201 M+, 172 M+-CHO

EXAMPLE 2

4-p-Fluorophenyl-3-hydroxymethylpyridine

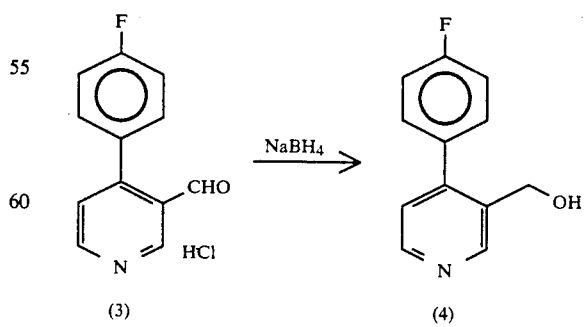

Solid sodium borohydride (2 g; 0.05 moles) was added portionwise to a solution of aldehyde hydrochloride (3; 5 g; 0.02 moles) in methanol (80 ml) at 0° C. After stirring for 30 minutes, the solvent was removed under reduced pressure and the residue partitioned between diethylether and 10% aqueous sodium hydroxide solution. The organic layer was washed with brine, dried (MgSO₄) and evaporated to give the desired alcohol (4) as a brown oil which crystallised slowly (4.22 g; 99% yield).

m.p.: 85–87° C.

nmr (CDCl₃): $\delta$8.70, (s), 1H $\delta$8.45, (d), 1H $\delta$7.50,–7.10, (m) 5H $\delta$4.65, (s), 2H $\delta$4.20, (broad s), 1H

EXAMPLE 3

4-p-Fluorophenyl-3-hydroxymethyl-1-methyl-pyridinium bromide

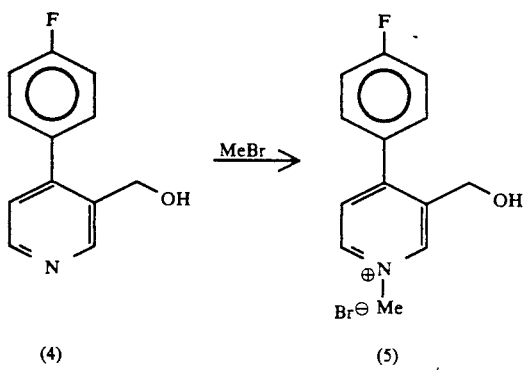

A solution of the pyridine (4; 3.4 g; 0.017 moles) in acetone (25 ml) at 0° C. was treated with excess methylbromide. The vessel was stoppered and the mixture was stirred at room temperature for 3 days. The precipitated pyridinium bromide (5) was collected as a light brown solid (4.3 g; 86%).

m.p.: 194–7° C.

nmr (DMSO): $\delta$9.10, (s), 1H $\delta$9.00, (d), 1H $\delta$8.10, (d), 1H $\delta$7.75,–7.40, (m) 4H $\delta$5.95, (t), 1H $\delta$4.60, (d), 2H $\delta$4.45, (s), 3H

EXAMPLE 4

($\pm$)-cis-4-p-Fluorophenyl-3-hydroxymethyl-1-methyl-piperidine

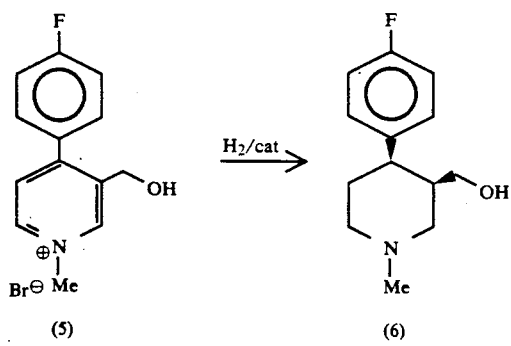

The quarternary salt (5; 1.45 g; 0.005 moles) in ethanol (50 ml) was hydrogenated over Adam's catalyst (150 mg) at atmospheric pressure and room temperature for 4 hours. After removal of the catalyst, the solvent was removed under reduced pressure and the residue partitioned between dichloromethane and 10% aqueous sodium carbonate solution. The organic layer was washed with brine, dried and evaporated. Column chromatography of the crude product (Al₂O₃: Activity II; EtOAc) afforded the desired piperidine (6) as a pale yellow solid (0.4 g; 37%).

m.p.: 87–9° C.

nmr (CDCl₃) $\delta$7.30–6.95, (m), 4H $\delta$3.70–3.50, (m), 2H $\delta$3.20–3.05, (m), 2H $\delta$2.90–2.80, (m), 1H $\delta$2.60–2.40, (m), 2H $\delta$2.30, (s), 3H $\delta$2.20–2.05, (m), 1H $\delta$1.80–1.70, (m), 2H M/e: 223 (M+), 204 (M+—F), 192 (M+—CH₂OH)

EXAMPLE 5

($\pm$)-cis-4-p-Fluorophenyl-3-hydroxymethyl-1-methyl-piperidine

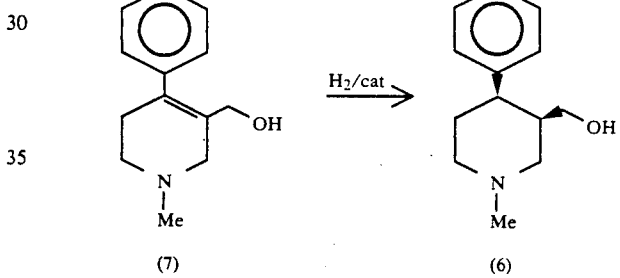

A solution of the quaternary salt (5: 1 g: 0.0034 moles) in methanol (10 ml) at 0° C. was treated portionwise with solid sodium borohydride (250 mg; 0.0066 moles) and the mixture was stirred at 0° C. for 45 minutes. The solvent was removed under reduced pressure the residue partitioned between ethyl acetate and 10% aqueous sodium hydroxide solution. The organic layer was washed with brine, dried (MgSO₄) and evaporated. This gave the allylic alcohol (7) as a dark oil which crystallised slowly (0.79 g; 100%).

nmr (CDCl₃) $\delta$7.15–6.95, (m), 4H $\delta$3.95, (s), 2H $\delta$3.20–3.15, (m), 2H $\delta$2.65–2.55, (m), 2H $\delta$2.50–2.40, (m), 2H $\delta$2.35, (s), 3H M/e: 221 (M+), 202 (M+—F), 190 (M+—CH₂OH)

The allylic alcohol (7; 0.7 g; 0.003 moles) in ethanol (20 ml) was hydrogenated over Adam's catalyst (100 mg) at atmospheric pressure and room temperature for 5 hours. Ethanolic HCl (2.5 M; 1.27 ml) was then added, and hydrogenation continued for 2 hours.

After removal of the catalyst, the solvent was removed under reduced pressure, and the residue was subjected to analysis by gas chromatography/mass spectrometry. This showed the desired alcohol to be present in a similar proportion to that found in the crude product obtained in Example 4.

We claim:

1. A process for preparing a compound of formula (I):

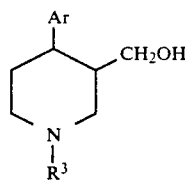

in which Ar represents an aryl or substituted aryl group and $R^3$ represents an alkyl group, which comprises;

i) reducing a compound of formula (V)

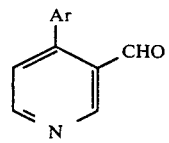

to form a compound of formula (IV)

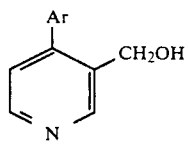

in which Ar is as defined in formula (I);

ii) quaternising the compound of formula (IV) with an alkyl halide of formula $R^3$-Hal, where $R^3$ is as defined in formula (I) and Hal is a halogen atom, to form a compound of formula (II)

and 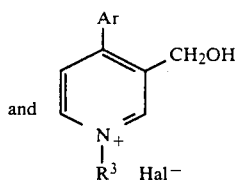

and iii) reducing the compound of formula (II) to produce a compound of the formula (I).

2. A process according to claim I in which Ar represents phenyl optionally substituted by one or more groups selected from hydrogen, $C_{1-6}$ alkyl, $C_{1-6}$ alkoxy, trifluoro $C_{1-6}$ alkyl, hydroxy, halogen, methylthio or phenyl $C_{1-6}$ alkyloxy, and $R^3$ represents $C_{1-6}$ alkyl.

3. A process according to claim 2 in which Ar represents fluorophenyl.

4. A process according to claim 3 in which $R^3$ represents methyl.

5. A process according to claim 1 in which Hal represents chlorine or bromine.

6. A process according to claim 1 in which the reduction is carried out by catalytic hydrogenation.

7. A process for preparing a compound of formula (I)

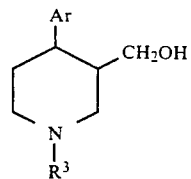

in which Ar represents an aryl or substituted aryl group and $R^3$ represents an alkyl group, which comprises:

i) reducing a compound of formula (V)

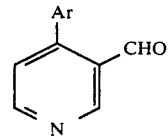

to form a compound of formula (IV)

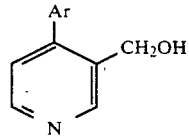

in which Ar is as defined in formula (I);

ii) quaternising the compound of formula (IV) with an alkyl halide of formula $R^3$-Hal, where $R^3$ is as defined in formula (I) and Hal is a halogen atom, to form a compound of formula (II)

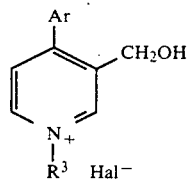

iii) reducing the compound of formula (II) to form a compound of formula (III)

and 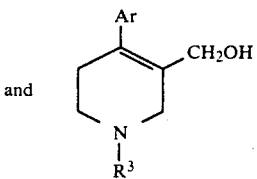

and iv) reducing the compound of formula (III).

* * * * *

UNITED STATES PATENT AND TRADEMARK OFFICE
CERTIFICATE OF CORRECTION

PATENT NO. : 5,039,803

DATED : August 13, 1991

INVENTOR(S) : Paul Smith, et al.

It is certified that error appears in the above-identified patent and that said Letters Patent is hereby corrected as shown below:

Title page items:

[63] Continuation-in-part of Ser. No. 209,873, Jun. 22, 1988, abandoned.

[30] FOREIGN APPLICATION PRIORITY DATA
Jun. 23, 1987 [GB] United Kingdom . . . . 8714707

Signed and Sealed this

Second Day of March, 1993

*Attest:*

STEPHEN G. KUNIN

*Attesting Officer*    Acting Commissioner of Patents and Trademarks